(12) United States Patent
Park et al.

(10) Patent No.: US 7,251,853 B2
(45) Date of Patent: Aug. 7, 2007

(54) ROBOT CLEANER HAVING FLOOR-DISINFECTING FUNCTION

(75) Inventors: Jee-su Park, Osan (KR); Ju-sang Lee, Gwangju (KR); Jang-youn Ko, Gwangju (KR); Young-ik Cho, Gwangju (KR); Jeong-gon Song, Gwangju (KR)

(73) Assignee: Samsung Gwangju Electronics Co., Ltd., Gwangju (KR)

( * ) Notice: Subject to any disclaimer, the term of this patent is extended or adjusted under 35 U.S.C. 154(b) by 520 days.

(21) Appl. No.: 10/822,652

(22) Filed: Apr. 13, 2004

(65) Prior Publication Data

US 2005/0022330 A1 Feb. 3, 2005

(30) Foreign Application Priority Data

Jul. 29, 2003 (KR) ............... 10-2003-0052449

(51) Int. Cl.
*A47L 5/00* (2006.01)
(52) U.S. Cl. ............... 15/319; 15/339; 15/340.1
(58) Field of Classification Search ............ 15/319, 15/339, 340.1
See application file for complete search history.

(56) References Cited

U.S. PATENT DOCUMENTS

| | | | | |
|---|---|---|---|---|
| 2,590,152 A | * | 3/1952 | McGowan | 15/319 |
| 2,632,912 A | * | 3/1953 | Cuddeback | 15/339 |
| 2,681,467 A | * | 6/1954 | Reynolds | 15/339 |
| 4,907,316 A | | 3/1990 | Kurz | |
| 5,233,723 A | | 8/1993 | Hung | |
| 5,548,511 A | * | 8/1996 | Bancroft | 15/319 |
| 5,815,880 A | | 10/1998 | Nakanishi | |
| 5,959,423 A | | 9/1999 | Nakanishi et al. | |
| 6,459,955 B1 | | 10/2002 | Bartsch et al. | |
| 6,481,515 B1 | | 11/2002 | Kirkpatrick et al. | |

(Continued)

FOREIGN PATENT DOCUMENTS

CN 2139811 Y 8/1993

(Continued)

OTHER PUBLICATIONS

The Patent Office Search and Examination Report; Jul. 29, 2005; 10 pages.

(Continued)

*Primary Examiner*—Theresa T. Snider
(74) *Attorney, Agent, or Firm*—Blank Rome LLP (57) ABSTRACT

A robot cleaner for simultaneously and selectively performing automatic floor cleaning and automatic floor disinfection. The robot cleaner includes a body traveling automatically on a surface to be cleaned, a driving unit for driving a plurality of wheels provided under the body, and obstacle detecting sensors positioned to a front of the body for detecting an obstacle located ahead of a traveling direction. The robot cleaner also includes memory for storing position information of the obstacle detected by the obstacle detecting sensor, a dust vacuuming and collecting section installed to the body for vacuuming dust on a floor, and a disinfecting section installed under a bottom portion of the body for disinfecting the floor. The robot cleaner also includes a control section for controlling the driving unit to traverse the robot cleaner along a given traveling path, and also control the dust vacuuming and collecting section and the disinfecting section.

9 Claims, 7 Drawing Sheets

U.S. PATENT DOCUMENTS

| | | |
|---|---|---|
| 2003/0030398 A1 | 2/2003 | Jacobs et al. |
| 2004/0244138 A1* | 12/2004 | Taylor et al. .................. 15/319 |
| 2005/0022844 A1* | 2/2005 | Field et al. .................... 134/6 |

FOREIGN PATENT DOCUMENTS

| | | |
|---|---|---|
| CN | 2389761 Y | 8/2000 |
| DE | 38 03 825 A1 | 8/1989 |
| DE | 42 22 805 | 2/1994 |
| GB | 2 277 251 A | 10/1994 |
| GB | 2376537 A | 12/2002 |
| JP | 2-63772 | 10/1988 |
| JP | 6-55544 | 8/1994 |
| JP | 11-244206 | 9/1999 |
| JP | 2002-177175 | 6/2002 |
| JP | 2002-325708 | 11/2002 |
| WO | WO 02/062194 | 8/2002 |

OTHER PUBLICATIONS

Combined Search and Examination Report dated Sep. 29, 2004 for Application No. GB0409424.9.

Swedish Patent Office, Office Action dated Mar. 16, 2005, issued in connection with the corresponding application No. 0401937-8.

Russian Patent Office, Office Action issued in connection with corresponding Application No. 2004116815.

Chinese Patent Office, Office Action issued Nov. 18, 2005 with respect to Chinese Patent Application No. 200410035374.3 filed on Apr. 22, 2004.

Japanese Patent Office, Office Action issued Jun. 20, 2006 with respect to Japanese Patent Application No. 2004-46391 filed on Feb. 23, 2004.

* cited by examiner

ROBOT CLEANER HAVING FLOOR-DISINFECTING FUNCTION

REFERENCE TO RELATED APPLICATION

This application claims priority to Korean Patent Application No. 2003-52449, filed Jul. 29, 2003, in the Korean Intellectual Property Office, the disclosure of which is entirely incorporated herein by reference.

CROSS-REFERENCE TO RELATED APPLICATION

This application is related to copending (Korean Patent Application No. 10-2003-0013961, filed Mar. 6, 2003; U.S. application Ser. No. 10/682,484 (Korean Patent Application No. 10-2003-0029242, filed May 9, 2003); U.S. application Ser. No. 10/804,407 (Korean Patent Application No. 10-2003-0043244, filed Jun. 30, 2003); and U.S. application Ser. No. 10/887,918 (Korean Patent Application No. 10-2003-0052451, filed Jul. 29, 2003), whose disclosures are entirely incorporated herein by reference.

FIELD OF THE INVENTION

The present invention relates to a robot cleaner with a floor-disinfecting function, and more particularly, to a robot cleaner capable of simultaneously or selectively performing automatic floor cleaning or automatic floor disinfection.

BACKGROUND OF THE INVENTION

Generally, a robot cleaner is a self-propelled working machine moving in a logical manner to vacuum dust or small litter. The robot cleaner determines a distance to obstacles, such as furniture, office appliances, walls or the like, provided in a region, which has to be cleaned by using sensors. The robot cleaner selectively drives a pair of motors to prevent a collision or interference with the obstacle, so that it may automatically change direction to clean the region.

Figure 1:
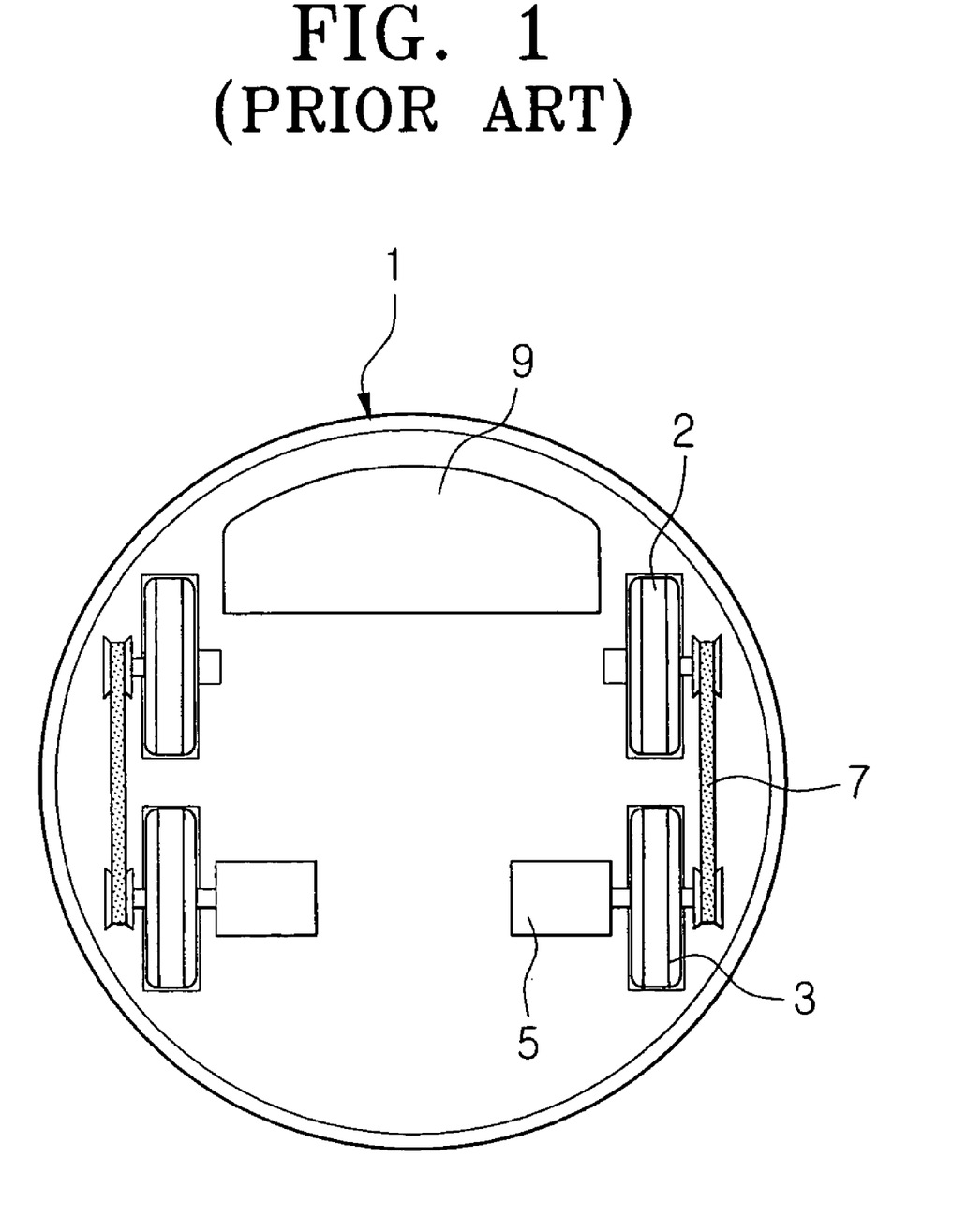
FIG. 1 is a drawing of a bottom view illustrating a bottom surface of a conventional robot cleaner.

Referring to FIG. 1, the robot cleaner includes a body 1, two driven wheels 2 each provided at both sides of a front lower portion of the body, two driving wheels 3 each provided at both sides of a rear lower portion of the body, a pair of motors 5 for driving the two rear driving wheels 3, and a timing belt 7 for transferring a driving force to the front driven wheels 2. The robot cleaner also includes a suction port 9 provided at a front end portion of the body 1 for suction of dust or small litter. The suction port 9 is driven by a predetermined driving motor (not shown).

The robot cleaner constructed as described above, automatically changes a traveling direction by selectively driving a pair of motors 5 while operating the suction port 9 to clean the region. Since conventional robot cleaners vacuum dust or small litter on the floor through the suction port 9 while traveling across a cleaning surface, the robot cleaner cannot disinfect bacteria or viruses that may exist on the floor. In order to disinfect the surface of the floor, a user cleans the floor again with a boiled wet dust cloth, which can be cumbersome. Thus, a heretofore unaddressed need exists in the industry to address the aforementioned deficiencies and inadequacies.

SUMMARY OF THE INVENTION

Accordingly, the present invention solves the above-mentioned problems occurring in the prior art, and, an aspect of the present invention is to provide a robot cleaner capable of simultaneously or selectively performing automatic floor cleaning and automatic floor disinfection.

In order to accomplish that aspect, a robot cleaner is provided which includes a body automatically traveling on a surface to be cleaned. A driving unit for driving a plurality of wheels is provided under the body. An obstacle detecting sensor is provided to a front of the body for detecting an obstacle positioned ahead of a traveling direction, and memory for storing position information of the obstacle detected by the obstacle detecting sensor. A dust vacuuming and collecting section is installed in the body for drawing in dust on a floor. A disinfecting section is installed under a bottom portion of the body for disinfecting the floor. A control section for controlling the driving unit to traverse the robot cleaner along a given traveling path, and controls the dust vacuuming and collecting section along with the disinfecting section. The disinfecting section may operate simultaneously with or separately from the dust vacuuming and collecting section. The disinfecting section includes a disinfection lamp, a receptacle chamber formed on a bottom of the body for accommodating the disinfection lamp, and a transparent window detachably engaged to the receptacle chamber through which the disinfection lamp radiates a light on the floor. The disinfecting section may be installed to one front portion of the bottom of the body, or may be installed between the driving unit and the dust vacuuming and collecting section under the bottom of the body.

In an alternative embodiment, the disinfecting section may be installed to one rear portion of the bottom of the body, or may be installed to left and right sides of the bottom of the body.

The driving unit may include a pair of motors installed to the body and driven by respectively by supplied power sources. A pair of driving wheels is rotated by the pair of driving motors. A pair of driven wheel is followed by the pair of driving wheels and a transmission means drives the driving wheels and the driven wheels. The transmission means may be a timing belt.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWING FIGURES

The above and other aspects, features and advantages of the present invention will be more apparent with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 2:
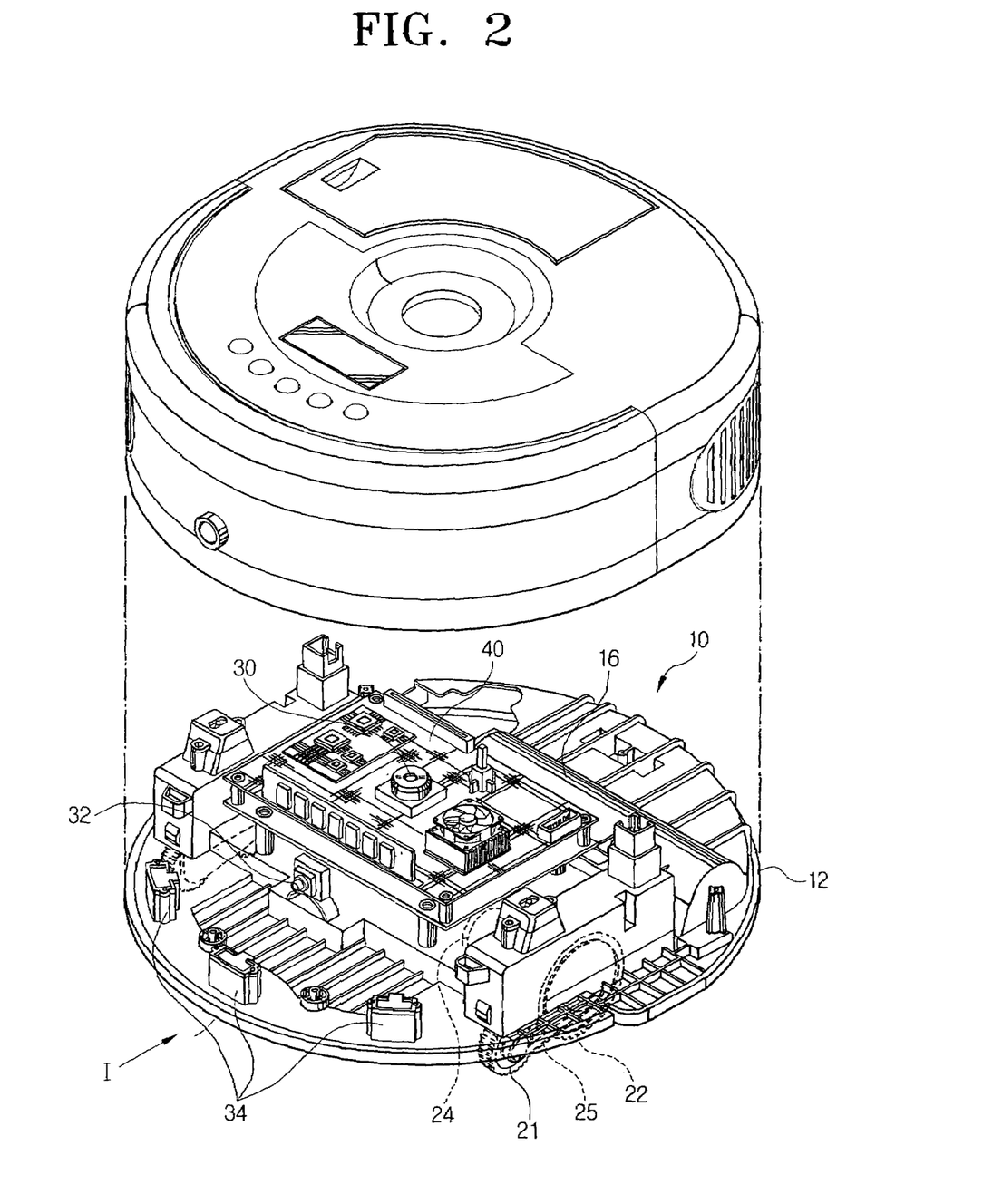
FIG. 2 is a drawing of a perspective view illustrating a structure of a robot cleaner with a floor-disinfecting function according to an embodiment of the present invention.
Figure 3:
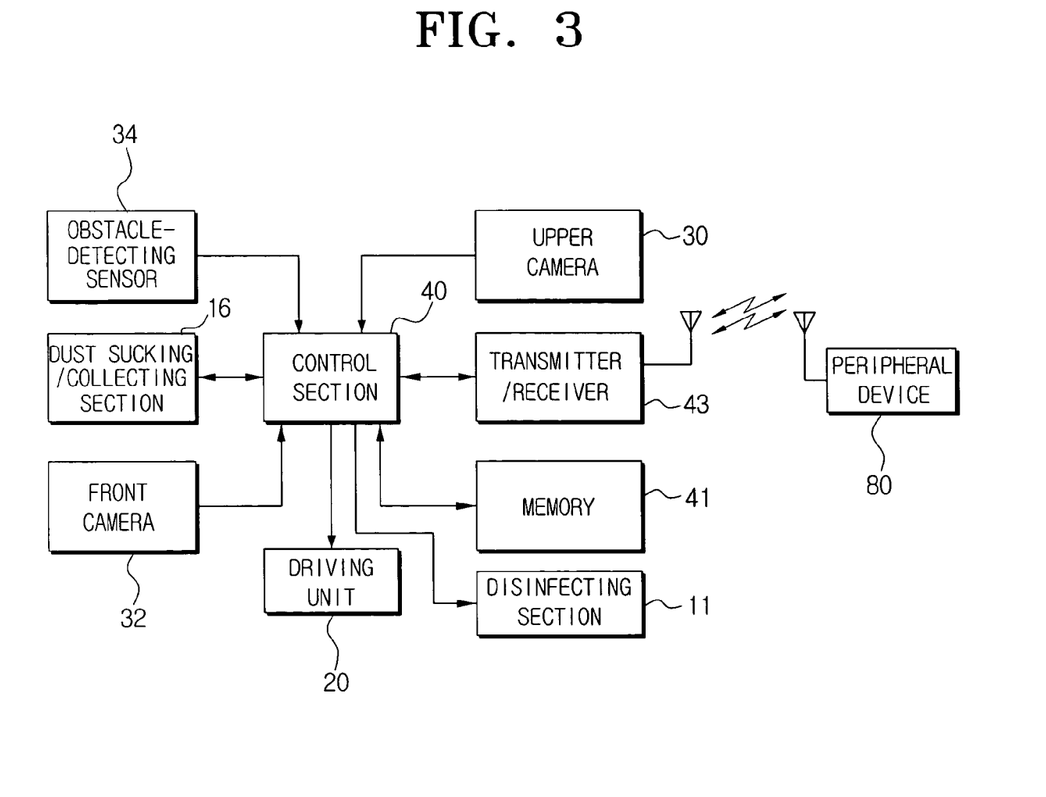
FIG. 3 is a block diagram showing a control of a robot cleaner according to an embodiment of the present invention.

Hereinafter, embodiments of the present invention are described with reference to the accompanying drawings. FIG. 2 is a perspective view illustrating a structure of a robot cleaner with a floor-disinfecting function according to the present invention, and FIG. 3 is a block diagram showing a control of a robot cleaner according to the present invention. Reference numeral I denotes a front of the robot cleaner. Referring to FIGS. 2 and 3, the robot cleaner includes a body 12, a dust vacuuming and collecting section 16, a driving unit 20, an upper camera 30, a front camera 32, obstacle-detecting sensors 34, a control section 40, a disinfecting section 11, memory 41, and a transmitter receiver 43.

The dust vacuuming and collecting section 16 is installed in the body 12 for vacuuming and collecting dust on a floor. The dust vacuuming and collecting section 16 may be constructed in numerous ways. For example, the dust vacuuming and collecting section 16 may include a suction motor (not shown), and a dust-collecting chamber for collecting dust drawn in through a suction port or pipe facing to the floor. The driving unit 20 includes two driven wheels 21 provided at both sides of a front portion of the body, two driving wheels 22 provided at both sides of a rear portion of the body, a pair of motors 24 for driving two rear driving wheels 22, respectively, and a transmission means 25 for transferring a driving force to the front driven wheels 21. The transmission means 25 includes a timing belt, but may include a gear pulley.

The driving units 20 rotate respectively motors 24 in forward or reverse directions per a control signal from the control section 40. A running direction is determined by controlling differently a revolution of the respective motors 24. The front camera 32 is located in the body 12 for taking a front image of the body 12 and outputs that image to the control section 40. The upper camera 30 is located in the body for taking a rear image of the body 12 and outputs that image to the control section 40. In another embodiment, a fish-eye lens (not shown) is applied to the upper camera 30. The construction of the fish-eye lens is disclosed in Korean Unexamined Patent Publication No. 1996-7005245, Korean Unexamined Patent Publication No. 1997-48669, and Korean Unexamined Patent Publication No. 1994-22112, and is commercially available from several lens manufacturers.

The obstacle detecting sensors 34 are provided around the body at a given interval in such a manner that they can emit a signal outwardly and receive a reflected signal. In an alternative embodiment, the obstacle-detecting sensor 34 may be an ultrasonic wave sensor which emits ultrasonic waves and receives the reflected ultrasonic waves. The obstacle-detecting sensor 34 is used to measure a distance from the body 12 to an obstacle or wall.

A traveling distance detecting sensor (not shown) connected to the control section 40 may include a revolution detecting sensor (not shown) for detecting a revolution of the driving wheels 22 or the driven wheels 21. For example, the revolution-detecting sensor (not shown) may include an encoder for detecting the revolution of the motor 24.

FIGS. 4A-4D are perspective views illustrating robot cleaners with a floor-disinfecting function according to embodiments of the present invention. The disinfecting section 11 will now be described with reference to FIGS. 4A-4D. The disinfecting section 11 includes a disinfection lamp 55, a receptacle chamber 57 and a transparent window 59. The disinfection lamp 55 is a general ultraviolet disinfection lamp which is commercially available. Such a lamp disinfects various viruses existing on a surface of a floor, the detailed description of which will be omitted herein.

The receptacle chamber 57 is a space to accommodate the disinfection lamp 55, and is formed in a groove shaped on a bottom surface of the robot cleaner 10. The receptacle chamber 57 may be formed in an elliptical groove shaped to comply with the shape of the disinfection lamp 55. The transparent window 59 is detachably engaged to the receptacle chamber 57 so that the disinfection lamp 55 radiates a light on the surface of the floor. Also, the transparent window protects the disinfection lamp 55 from protrusions or substances existing on the floor.

Figure 4A:
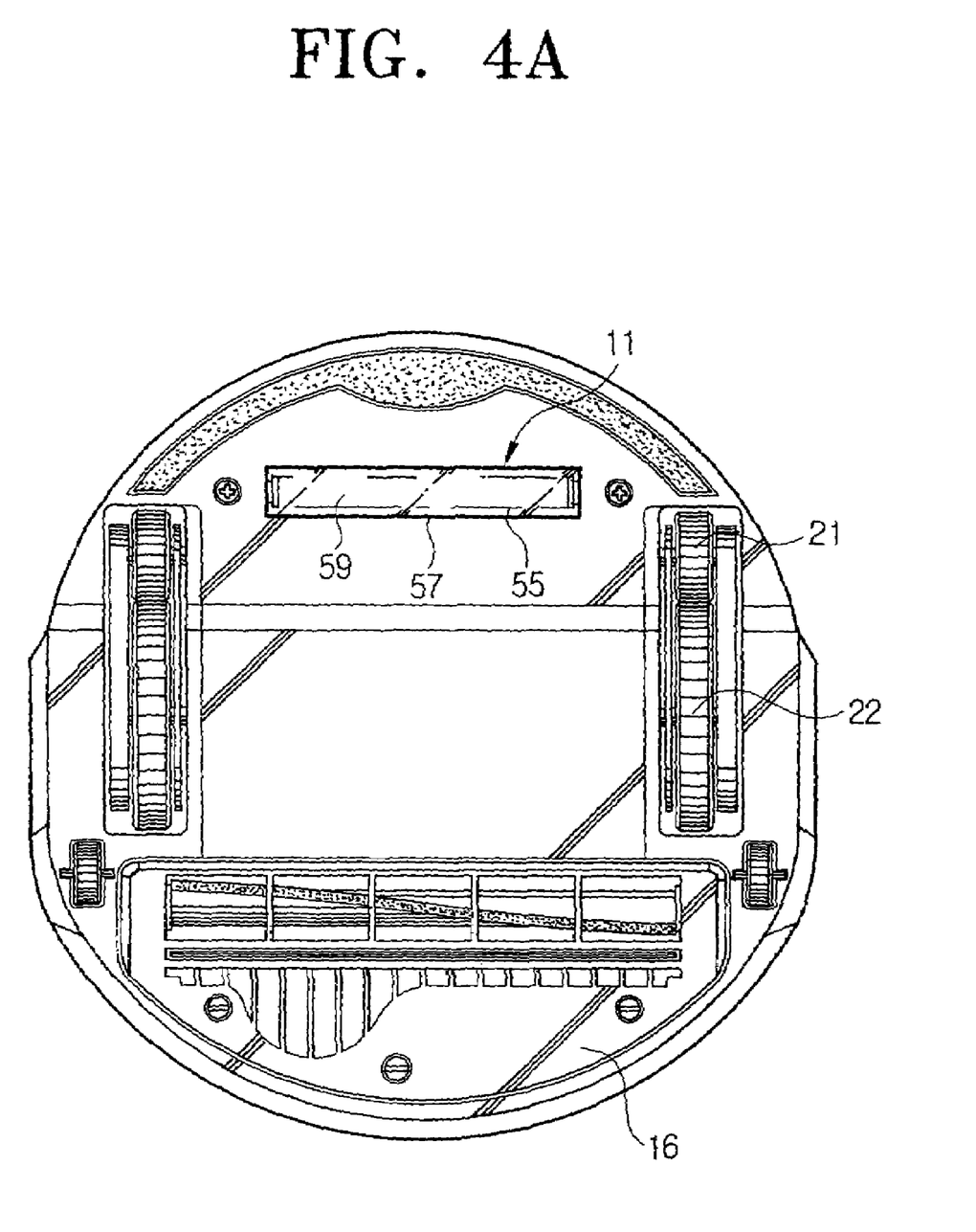
FIGS. 4A to 4D are drawings of perspective views illustrating robot cleaners with a floor-disinfecting function according to an embodiment of the present invention.
Figure 4B:
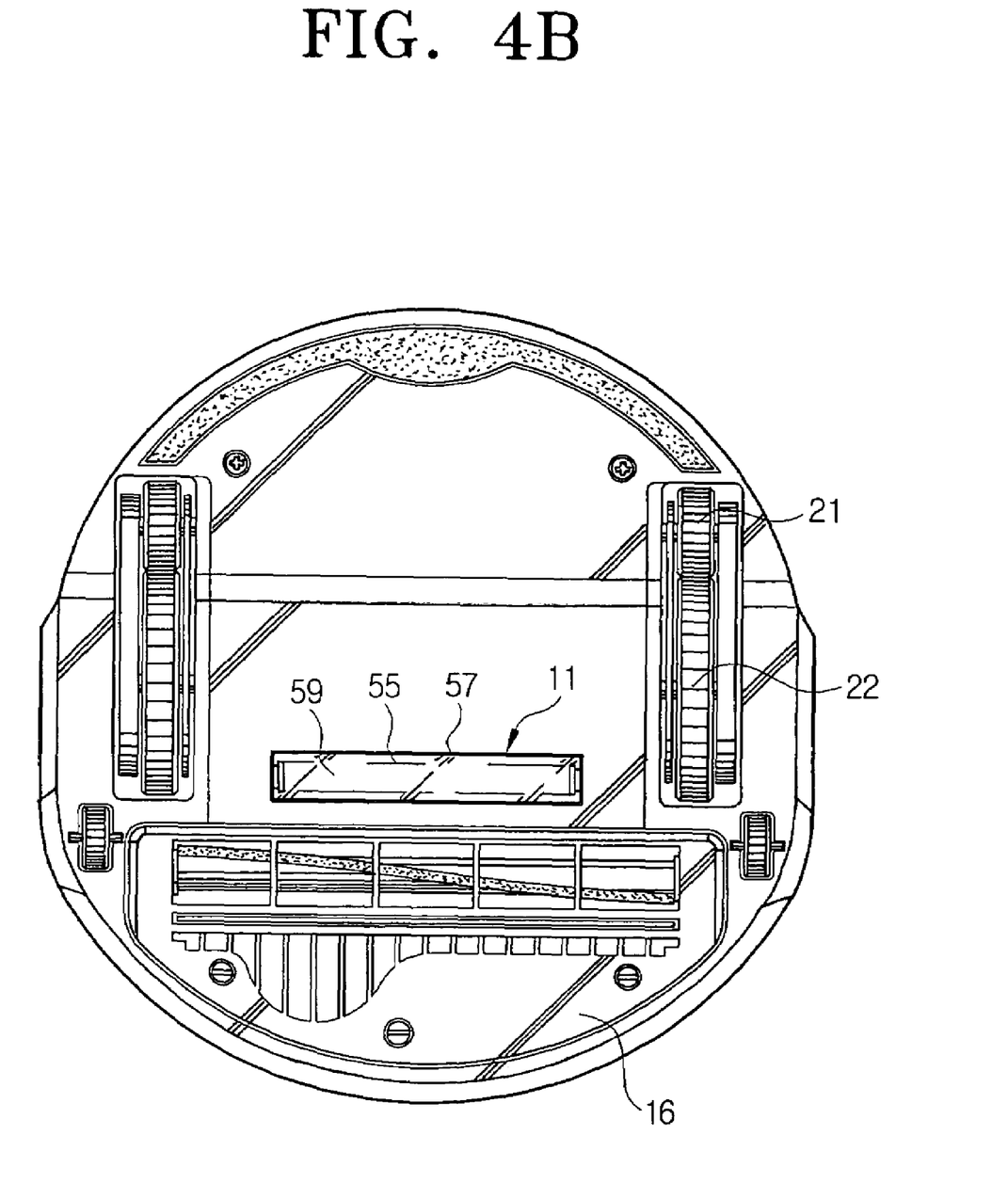
Figure 4C:
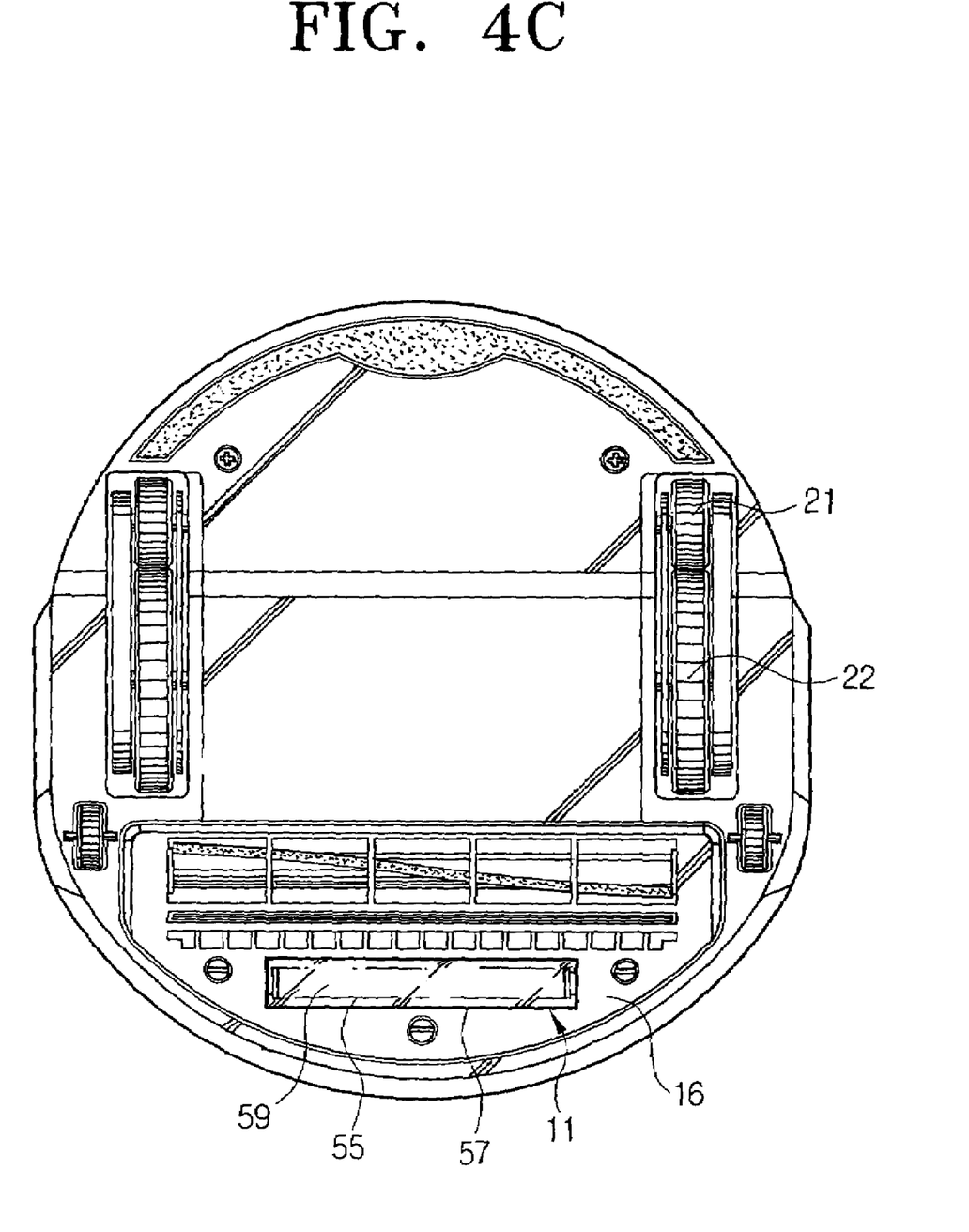
Figure 4D:
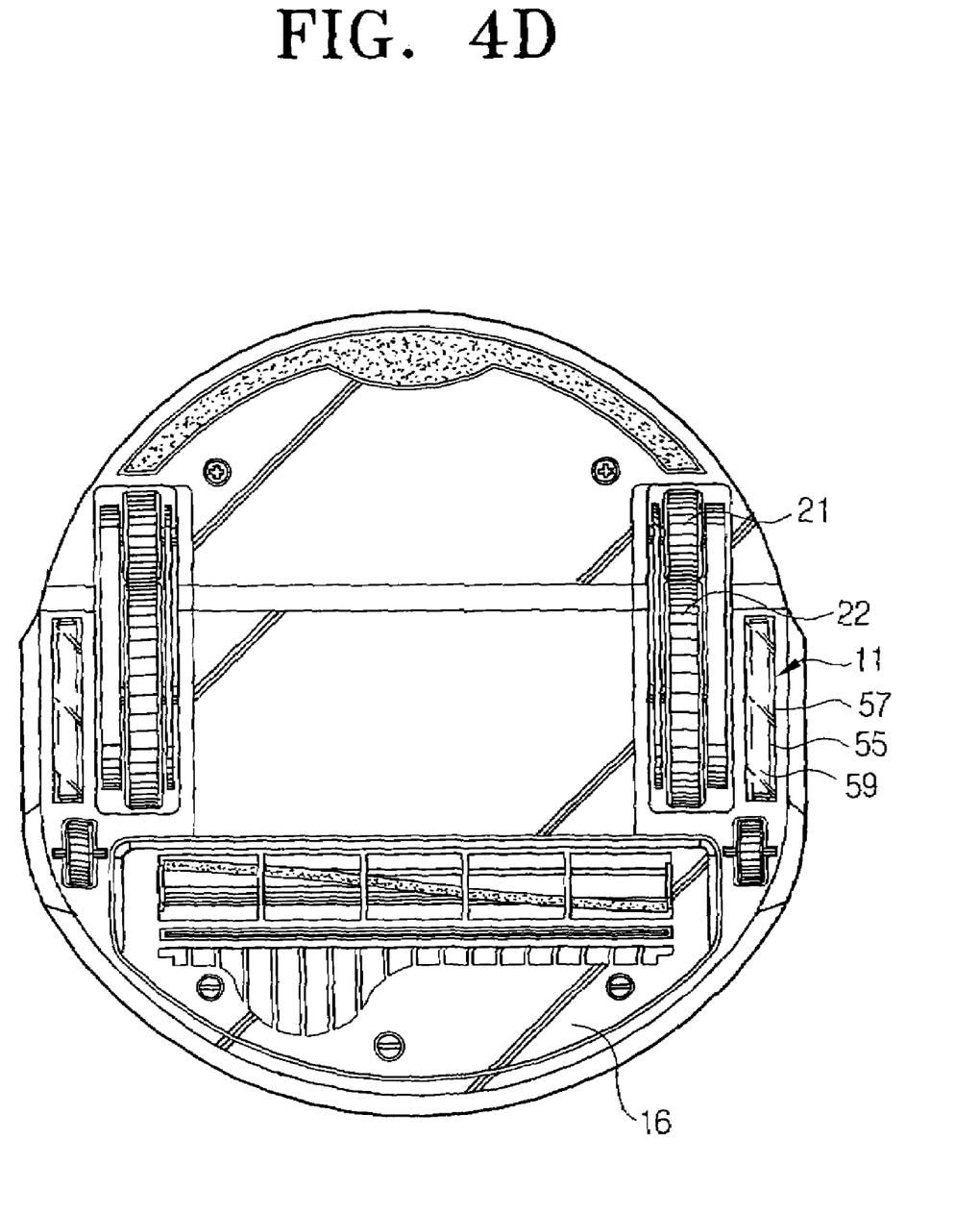

The disinfecting section 11 may be installed to a front portion of a bottom surface of the body 12 (FIG. 4A), or may be installed between the driving unit 20 and the dust vacuuming and collecting section 16 under the bottom surface of the body 12 (FIG. 4B). The disinfecting section 11 may be installed to a rear portion of a bottom surface of the body 12 (FIG. 4C), or may be installed to left and right sides of the bottom surface of the body 12 (FIG. 4D). In addition, the installed position of the disinfecting section 11 may be selected wherever the disinfection lamp 55 can radiate the light on the floor. The disinfecting section 11 can operate simultaneously with the operation of the dust vacuuming and collecting section 16, or can operate independently of the dust vacuuming and collecting section 16. Also, the memory 41 stores the upward image taken by the camera 30, and contributes to the acquisition of position information or traveling information (referring to FIG. 3).

The transmitter/receiver 43 transmits data to a peripheral device 80 through a transmitter and receiver (not shown) installed in the control section 40, and also transmits a signal from the peripheral device 80, which is received by the transmitter and receiver (not shown), and transmitted to the control section 40. The peripheral device 80 is a wireless relay (not shown) or a remote controller (not shown) to input and output data. The peripheral device 80 may be a remote controller. The control section 40 processes the signal received through the transmitter/receiver 43 to control each element of the robot cleaner. Where the body 12 is provided with a key input unit (not shown) and a plurality of keys for operating functions of the robot cleaner, the control section 40 processes key signals inputted from the key input unit.

The control section 40 controls the driving unit 20 to traverse a working region along a traveling pattern. Also, the control section 40 generates an image map on the upward region from the image taken by the upper camera 30. Alternatively, if a working instruction is wirelessly received from the key input unit or the exterior, it may be set to perform the preparation of the image map prior to cleaning work.

After preparing the image map, the control section 40 perceives its position by use of the image map. Specifically, if a signal requesting cleaning work is wirelessly received by the key input unit or the exterior, the control section 40 perceives the present position of the robot cleaner by comparing the stored image map with the present image inputted from the upper camera 30, or the upper camera 30 and the front camera 32, and thus controls the driving unit 20 according to a target traveling path from the perceived position. The signal requesting cleaning work includes the cleaning work or operational monitoring operation through the cameras 30 and 32.

When the robot cleaner travels along the target traveling path, the control section calculates a traveling error by use of a traveling distance measured by the encoder and the present position perceived and comparing the stored image map with the present image, and compensates the error to allow the driving unit 15 to trace the target traveling path.

While the robot cleaner 10 travels, the control section 40 simultaneously, or selectively, operates the dust vacuuming and collecting section 16 and the disinfecting section 11 according to the cleaning signal.

Accordingly, the disinfection lamp 55 of the disinfecting section 11 is supplied with power from a power supplier (not shown) provided in the body 12. The dust or litter existing on the floor is drawn into the body 12 through the suction motor (not shown) and the suction pipe, while purified air is discharged therefrom. As a result, the robot cleaner simultaneously, or selectively, cleans and disinfects the floor.

If the user inputs a signal for stopping the operation of the driving unit 20 to the peripheral device 80, the robot cleaner 10 can simultaneously, or selectively, perform the cleaning and disinfecting work for the floor at a standstill in a desired space. After the cleaning work or the disinfecting work is completed, if the user inputs the work stopping instruction to the robot cleaner through the peripheral device 80, the control section 40 of the robot cleaner 10 stops the cleaning and disinfecting work and returns the robot cleaner 10 to its initial position.

As described above, the robot cleaner with the disinfecting feature according to the present invention can simultaneously or selectively perform the cleaning and disinfecting work on the floor while it travels in a given space. While the invention has been shown and described with reference to certain embodiments thereof, it will be understood by those skilled in the art that various changes in form and details may be made therein without departing from the spirit and scope of the invention as defined by the appended claims.

What is claimed is:

1. A robot cleaner comprising:
   a body automatically traveling on a surface to be cleaned;
   a driving unit for driving a plurality of wheels provided under the body;
   at least one obstacle detecting sensor positioned to a front of the body for detecting an obstacle located ahead of a traveling direction;
   memory for storing position information of the obstacle detected by the obstacle-detecting sensor;
   a dust vacuuming and collecting section installed to the body for vacuuming dust on a floor;
   a disinfecting section installed under a bottom portion of the body for disinfecting the floor; and
   a control section controlling the driving unit to traverse the robot cleaner along a given traveling path and selectively operating the disinfecting section simultaneously with the dust vacuuming and collecting section and independently from the dust vacuuming and collecting section.

2. The robot cleaner as claimed in claim 1, wherein the disinfecting section includes
   a disinfection lamp;
   a receptacle chamber formed on a bottom of the body for accommodating the disinfection lamp; and
   a transparent window detachably engaged to the receptacle chamber, through which the disinfection lamp irradiates a light on the floor.

3. The robot cleaner as claimed in claim 1, wherein the disinfecting section is installed to one front portion of the bottom of the body.

4. The robot cleaner as claimed in claim 1, wherein the disinfecting section is installed between the driving unit and the dust vacuuming and collecting section under the bottom of the body.

5. The robot cleaner as claimed in claim 1, wherein the disinfecting section is installed to one rear portion of the bottom of the body.

6. The robot cleaner as claimed in claim 1, wherein the disinfecting section is installed to left and right sides of the bottom of the body.

7. The robot cleaner as claimed in claim 1, wherein the driving unit includes
   a pair of motors installed in the body and driven by supplied power;
   a pair of driving wheels rotated by the pair of driving motors;
   a pair of driven wheels followed by the pair of driving wheels; and transmission means for driving the driving wheels and the driven wheels.

8. The robot cleaner as claimed in claim 1, wherein the transmission means is a timing belt.

9. A method of operating a robot cleaner, the robot cleaner having a body with a plurality wheels, a driving unit, at least one obstacle detecting sensor, a memory for storing position information of obstacles detected by the obstacle detecting sensor, a dust vacuuming and collecting section in the body, a disinfecting section in the body, and a control section for controlling the driving unit, the dust vacuuming and collecting section, and the disinfecting section, comprising the steps of:
   automatically driving the robot cleaner on a surface to be cleaned along a given travel path;
   detecting obstacles in the travel path using the obstacle detecting sensor; and
   disinfecting the surface being cleaned by selectively operating the disinfecting section simultaneously with and independently of suctioning dust from the surface being cleaned into the dust vacuuming and collecting section.

* * * * *